US007548320B2

(12) United States Patent
Chan et al.

(10) Patent No.: US 7,548,320 B2
(45) Date of Patent: Jun. 16, 2009

(54) OPTICAL IMAGE MEASURING APPARATUS

(75) Inventors: Kinpui Chan, Yamagata (JP); Masahiro Akiba, Yamagata (JP); Yasufumi Fukuma, Tokyo (JP); Hiroyuki Otsuka, Tokyo (JP); Hisashi Tsukada, Tokyo (JP)

(73) Assignee: Kabushiki Kaisha Topcon, Itabashi-Ku (JP)

( * ) Notice: Subject to any disclaimer, the term of this patent is extended or adjusted under 35 U.S.C. 154(b) by 284 days.

(21) Appl. No.: 11/091,478

(22) Filed: Mar. 29, 2005

(65) Prior Publication Data

US 2005/0219544 A1 Oct. 6, 2005

(30) Foreign Application Priority Data

Mar. 30, 2004 (JP) ............................. 2004-100741

(51) Int. Cl.
*G01B 11/02* (2006.01)
(52) U.S. Cl. ..................................................... 356/497
(58) Field of Classification Search .................. 356/479, 356/484, 485, 489, 492, 497, 495, 498, 503, 356/511, 512
See application file for complete search history.

(56) References Cited

U.S. PATENT DOCUMENTS

| 4,596,466 | A | * | 6/1986 | Ulrich ......................... | 356/497 |
|---|---|---|---|---|---|
| 4,995,726 | A | * | 2/1991 | Fujita et al. ................. | 356/489 |
| 5,471,303 | A | * | 11/1995 | Ai et al. ...................... | 356/497 |
| 5,589,938 | A | * | 12/1996 | Deck .......................... | 356/497 |
| 5,909,279 | A | * | 6/1999 | Pepper et al. ............... | 356/479 |
| 6,088,100 | A | * | 7/2000 | Brenan et al. ............... | 356/456 |
| 6,195,168 | B1 | * | 2/2001 | De Lega et al. ............ | 356/497 |
| 6,198,540 | B1 | * | 3/2001 | Ueda et al. .................. | 356/479 |
| 6,268,921 | B1 | | 7/2001 | Seitz et al. | |

(Continued)

FOREIGN PATENT DOCUMENTS

JP 3245135 10/2001

(Continued)

OTHER PUBLICATIONS

V.X.D. Yang et al., "Micromachined array tip for multifocus fiber-based optical coherence tomography," Optical Society of America, Optics Letters, Aug. 1, 2004, vol. 29, No. 15, pp. 1754-1756.*

(Continued)

*Primary Examiner*—Patrick J Connolly
*Assistant Examiner*—Scott M Richey
(74) *Attorney, Agent, or Firm*—Edwards Angell Palmer & Dodge LLP

(57) ABSTRACT

An optical image measuring apparatus including: a beam splitter (4) for dividing a light beam into signal light (S) and reference light (R); beam splitters for dividing the reference light (R) into plural reference light beams frequency shifters for shifting frequencies of the reference light beams by different amounts; and reflector plates arranged at different distances from an object to be measured (O). The reference light beams and the signal light (S) reflected by the object to be measured in depth regions are superimposed on each other to thereby produce interference light. CCD cameras receive the interference light component and convert the interference light component into electrical signals to output the signals. A computer forms images in depth regions corresponding to the interference light components based on the electrical signals.

8 Claims, 6 Drawing Sheets

U.S. PATENT DOCUMENTS

| | | | |
|---|---|---|---|
| 6,285,456 B1* | 9/2001 | Narumi | 356/497 |
| 6,882,431 B2* | 4/2005 | Teich et al. | 356/497 |
| 6,924,898 B2* | 8/2005 | Deck | 356/512 |
| 7,061,620 B2* | 6/2006 | Bonnet | 356/489 |
| 7,241,982 B2* | 7/2007 | Chan et al. | 250/208.1 |
| 2002/0044713 A1* | 4/2002 | Hung | 385/15 |
| 2004/0156053 A1* | 8/2004 | Wolleschensky et al. | 356/485 |
| 2005/0190374 A1* | 9/2005 | Chan et al. | 356/497 |
| 2005/0206906 A1* | 9/2005 | Chan et al. | 356/497 |
| 2005/0280827 A1* | 12/2005 | Potma et al. | 356/485 |

FOREIGN PATENT DOCUMENTS

| | | |
|---|---|---|
| JP | 2001-330558 | 11/2001 |
| WO | 03/007811 | 1/2003 |

OTHER PUBLICATIONS

A.Gh. Podoleanu et al., "Simultaneous en-face imaging of two layers in the human retina by low-coherence reflectometry," Optical Society of America, Optics Letters, Jul. 1, 1997, vol. 22, No. 13, pp. 1039-1041.*

Libo Yuan, "White-light interferometric fiber-optic strain sensor from three-peak-wavelength broadband LED source," Applied Optics, vol. 36, No. 25, Sep. 1, 1997, pp. 6246-6250.*

European Search Report in connection with European Patent Application No. 05006897, dated Jul. 21, 2005.

N. Tanno, "The imaging technic of the optical coherence tomography and its application to living organism image;" *KOGAKU* (*Japanese Journal of Optics*); vol. 28, No. 3, pp. 116-125 and cover page (1999)./Discussed in the specification.

Yoshizawa, et al. (editors), "Optical Heterodyne Technology," the article by T. Nakajima, "Principle and application of the optical heterodyne method;" *New Technology Communications*, revised edition, p. 1-11 and cover page (7 sheets total)./Discussed in the specification.

M. Akiba, et al."Full-field optical coherence tomography by two-dimensional heterodyne detection with a pair of CCD cameras;" *Optics Letters*, vol. 28, No. 10, pp. 816-818, May 2003./ Discussed in the specification.

K.P. Chan, et al. "Micrometre-resolution, optical imaging of objects through highly scattering media using a heterodyne detector array;" *Electronics Letters*, vol. 30, No. 21, pp. 1753-1754, Oct. 1994./ Discussed in the specification.

* cited by examiner

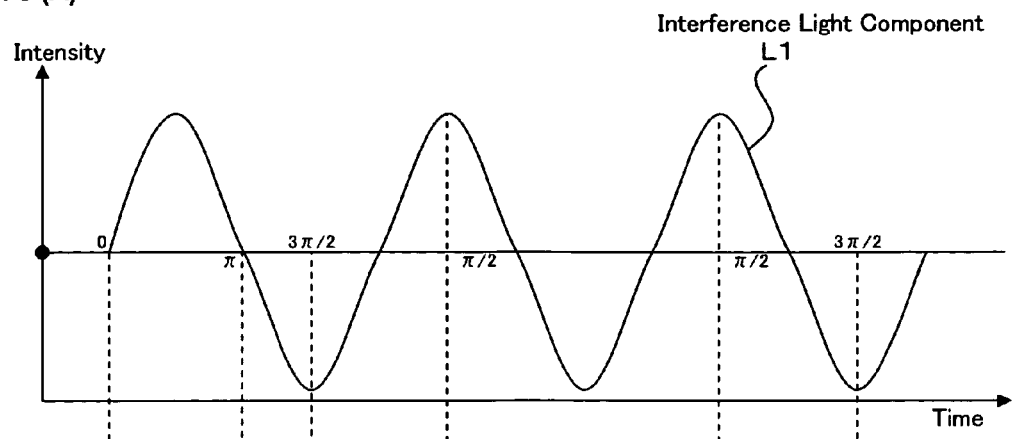
FIG. 3 (A)
FIG. 3 (B)
m1(t)
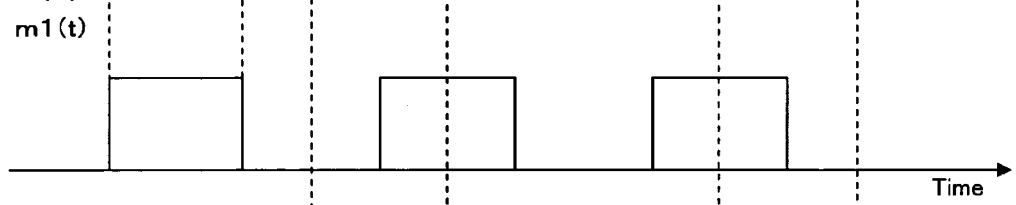
FIG. 3 (C)
m2(t)
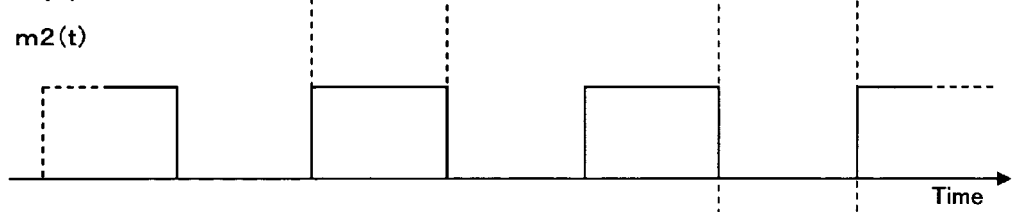
FIG. 3 (D)
m3(t)

m1(t)

m2(t)

m3(t)

m1(t)

m2(t)

m3(t)

OPTICAL IMAGE MEASURING APPARATUS

BACKGROUND OF THE INVENTION

1. Field of the Invention

The present invention relates to an optical image measuring apparatus employing a structure in which an object to be measured which is particularly a light scattering medium is irradiated with a light beam and a surface form or inner form of the object to be measured is measured based on a reflected light beam or a transmitted light beam to produce an image of a measured form. More particularly, the present invention relates to an optical image measuring apparatus for measuring the surface form or inner form of the object to be measured by using an optical heterodyne detection method to produce the image of the measured form.

2. Description of the Related Art

In recent years, attention has been given to optical imaging techniques for producing an image of a surface or inner portion of an object to be measured using a laser light source or the like. In contrast to the conventional X-ray CT technique, optical imaging technique is not hazardous to human bodies. Therefore, its application to the field of biomedical imaging is highly desired.

An example of a typical method of the optical imaging technique is a low coherent interference method (also called "optical coherence tomography" or the like). This method uses the low coherence of a broad band light source having a wide spectral width, such as a super luminescent diode (SLD). According to this method, reflection light from an object to be measured or light transmitting therethrough can be detected with a superior distance resolution of μm order (for example, see Naohiro Tanno, Kogaku (Japanese Journal of Optics), Volume 28, No. 3, 116 (1999)).

FIG. 6 shows a fundamental structure of a conventional optical image measuring apparatus based on a Michelson interferometer, serving as an example of an apparatus using the low coherent interference method. An optical image measuring apparatus 100 includes a wide band light source 101, a mirror 102, a beam splitter (half mirror) 103, and a photo detector 104. An object to be measured 105 is made of a scattering medium. A light beam from the broad band light source 101 is divided by the beam splitter 103 into two parts, that is, a reference light R propagating to the mirror 102 and a signal light S propagating to the object to be measured 105. The reference light R is a light beam reflected by the beam splitter 103. The signal light S is a light beam transmitting through the beam splitter 103.

Here, as shown in FIG. 6, the propagating direction of the signal light S is set as a z-axis and a plane orthogonal to the propagating direction of the signal light S is defined as an x-y plane. The mirror 102 is shiftable in both of the forward and backward direction, as indicated by a double-headed arrow in FIG. 6 (z-scanning direction).

The reference light R is subjected to a Doppler frequency shift by z-scanning when it is reflected on the mirror 102. On the other hand, the signal light S is reflected from the surface of the object to be measured 105 and from the inner layers thereof when the object to be measured 105 is irradiated with the light. Because the object to be measured 105 is a scattering medium, the signal light S reflected from the object may include the multiple scattered light waves having random phases. The signal light reflected from the object to be measured 105 and the reference light reflected from the mirror 102 to be subjected to the frequency shift are superimposed on each other by the beam splitter 103 to produce an interference light.

In the image measurement using the low coherent interference method, interference occurs only when a difference in optical path length between the signal light S and the reference light R is within the coherent length, of the broad band light source 101, which is of the order of several μm to tens of μm. In addition, only the component of the signal light S where phase is correlated to that of the reference light R may interfere with the reference light R. That is, only the coherent signal light component of the signal light S selectively interferes with the reference light R. Based on these principles, the position of the mirror 102 is shifted by the z-scanning operation to vary the optical path length of the reference light R, so that a light reflection profile of the inner layers of the object to be measured 105 is measured. The interference light is detected by the photo detector 104 during each z-scan. An electrical signal (heterodyne signal) output from the photo detector 104 provides a backscatter profile of the inner layers of object to be measured 105, and a two-dimensional cross-sectional image of the object to be measured 105 is produced by scanning the signal lights S across the object to be measured 105 while recording the reflectance profile at each transverse position (see Naohiro Tanno, Kogaku (Japanese Journal of Optics), Volume 28, No. 3, 116 (1999)).

Assume that an intensity of the reference light R and an intensity of the signal light S which are superimposed by the beam splitter 103 are given by $I_r$ and $I_s$, respectively, and a frequency difference between the reference light R and the signal light S and a phase difference therebetween are given by $f_{if}$ and $\Delta\theta$, respectively. In this case, a heterodyne signal as expressed by the following expression is outputted from the photo detector (for example, Yoshizawa and Seta "Optical Heterodyne Technology (revised edition)", New Technology Communications (2003), p. 2).

$$i(t) \propto I_r + I_s + 2\sqrt{I_r I_s} \cos(2\pi f_{if} t + \Delta\theta) \quad (1)$$

The third term of the right side of the expression (1) indicates an alternating current electrical signal and the frequency $f_{if}$ thereof is equal to the frequency difference between the reference light R and the signal light S. The frequency $f_{if}$ of an alternating current component of the heterodyne signal is called a beat frequency or the like. The first and second terms of the right side of the expression (1) indicate the direct current components of the heterodyne signal and correspond to the background light intensity.

However, when the two-dimensional cross-sectional image is intended to be obtained by means of the conventional low coherent interference method, it is necessary to scan the signal light beam S across the object to be measured 105 and to successively detect reflection light waves from each transverse position. Therefore, the measurement of the object to be measured 105 can be time consuming. In addition, it is hard to shorten a measurement time in view of measurement fundamentals.

In views of such problems, an optical image measuring apparatus for shortening a measurement time has been proposed. FIG. 7 shows a fundamental structure of an example of such an apparatus. As shown in FIG. 7, an optical image measuring apparatus 200 includes a broad band light source 201, a mirror 202, a beam splitter (half mirror) 203, a two-dimensional photo sensor array 204 serving for light detection, and lenses 206 and 207. A light beam from the light source 201 is converted into a parallel light flux by the lenses 206 and 207 and a beam diameter thereof is increased thereby. Then, the parallel light flux is divided by the beam splitter 203 into two, that is, the reference light R and the signal light S. The reference light R is subjected to a Doppler frequency shift by z-scanning of the mirror 202. On the other hand, the signal light S is incident on the object to be measured 205 over a wide area of the x-y plane, as a consequence of a widened beam diameter. Therefore, the signal light S reflected from the object to be measured 205 contains information related to the surface and inner portion of the object to be measured 205 over a wide area. The reference light R and the signal light S are superimposed on each other by the beam splitter 103 and detected by the elements (photo sensors) arranged in parallel on the surface of the two-dimensional photo sensor array 204. Thus, it is possible to obtain a two-dimensional cross-sectional image of the object to be measured 205 in real time without scanning the signal lights.

An apparatus described by K. P. Chan, M. Yamada, and H. Inaba in Electronics Letters, Vol. 30, 1753 (1994) has been known as such a non-scanning type optical image measuring apparatus. In the apparatus described in the same document, a plurality of heterodyne signals outputted from a two-dimensional photo sensor array are inputted to signal processing systems arranged in parallel to detect the amplitude and phase of each of the heterodyne signals.

However, when spatial resolution of an image is intended to be improved, it is necessary to increase the number of elements of the array. In addition, it is necessary to prepare a signal processing system including the number of channels corresponding to the number of elements. Therefore, it is likely to be hard to actually use the apparatus in fields that require a high-resolution image, such as a medical field and an industrial field.

Thus, the inventors of the present invention proposed the following non-scanning type optical image measuring apparatus in JP 2001-330558 A (claims, specification paragraphs [0044], [0072] to [0077]. The optical image measuring apparatus according to the present proposal includes a light source for emitting a light beam, an interference optical system, and a signal processing portion. In the interference optical system, the light beam emitted from the light source is divided into two, that is, a signal light propagating through an examined object locating position in which an object to be examined is located, and a reference light propagating along an optical path different from an optical path passing through the examined object locating position. The signal light propagating through the examined object locating position and the reference light propagating along a different optical path are superimposed on each other to produce the interference light. The interference optical system includes a frequency shifter, light cutoff devices, and photo sensors. The frequency shifter shifts a frequency of the signal light and a frequency of the reference light relative to each other. In order to receive the interference light in the interference optical system, the interference light is divided into two parts. The light cutoff devices periodically cut off the two divided parts of the interference light to generate two interference light pulse trains with a phase difference of 90 degrees therebetween. The photo sensors respectively receive the two interference light pulse trains. The photo sensors each have a plurality of light receiving elements which are spatially arranged and each of which separately obtains a light receiving signal. The signal processing portion combines a plurality of light receiving signals obtained by each of the photo sensors to generate signals of the signal light which correspond to respective points of interest of a surface or inner layers of the object to be examined which is located in the examined object locating position on a propagation path of the signal light.

In the optical image measuring apparatus, the interference light in which the reference light and the signal light interfere with each other is divided into two parts and the two parts of the interference light are received by the two photo sensors (two-dimensional photo sensor arrays) and respectively sampled by the light cutoff devices disposed in fronts of both sensor arrays. A phase difference of $\pi/2$ is provided between sampling periods of the two divided parts of the interference light. Therefore, an intensity of the signal light and an intensity of reference light which compose background light of the interference light and phase quadrature components (sine component and cosine component) of the interference light are detected. In addition, an intensity of the background light included in the outputs from both the sensor arrays is subtracted from the outputs of both the sensor arrays to calculate two phase quadrature components of the interference light. An amplitude of the interference light is obtained based on a result obtained by calculation.

In addition, the inventors of the present invention have proposed the following optical image measuring apparatus in JP 3245135 B (claims and specification paragraphs [0072] to [0082]). The optical image measuring apparatus according to this proposal includes a light source for emitting a light beam and an interference optical system. In the interference optical system, the light beam emitted from the light source is divided into two, that is, signal light propagating through an examined object arrangement position in which an object to be examined is arranged and reference light propagating on an optical path different from an optical path passing through the examined object arrangement position. The signal light propagating through the examined object arrangement position and the reference light propagating on the different optical path are superimposed on each other to produce interference light in which the signal light and the reference light interfere with each other. The interference optical system includes a frequency shifter and an optical device. The frequency shifter shifts a frequency of the signal light and a frequency of the reference light relative to each other. The optical device is disposed on an optical path of at least one of the signal light and the reference light and periodically cuts off light. The cutoff frequency of the optical device is set to be equal to a frequency difference between the signal light and the reference light. According to the optical image measuring apparatus, the interference light can be sampled at the cutoff frequency equal to a beat frequency. Therefore, suitable optical heterodyne measurement is realized.

The optical image measuring apparatuses disclosed in JP 2001-330558 A (claims, specification paragraph [0044], [0072]~[0077]) and JP 3245135 B (claims, specification paragraph [0072]~[0082]) take an image of an object to be measured in a single depth region using interference light based on light reflected by (or transmitted through) the object to be measured in the signal depth region. Hence, in the case of taking images of the object to be measured in plural depth regions, it is necessary to scan the object to be measured for each depth region for measurement, so the measurement takes much time to complete.

SUMMARY OF THE INVENTION

The present invention has been made in view of the above-mentioned circumstances, and it is therefore an object of the present invention to provide an optical image measuring apparatus capable of taking images of an object to be measured in each of plural depth regions in parallel by producing interference light including components corresponding to the plural depth regions thereof and selectively detecting each component from the interference light.

In order to achieve the above-mentioned object, a first aspect of the present invention provides an optical image measuring apparatus, including: a light source for emitting a light beam; an interference optical system for producing interference light including a plurality of interference light components whose frequencies are different depending on depth regions of an object to be measured based on the light beam from the light source; a detection system for selectively detecting the interference light components from the produced interference light; and image forming means for forming images of the object to be measured in the depth regions corresponding to the interference light components based on the detected interference light components.

Further, according to a second aspect of the present invention, in the optical image measuring apparatus according to the first aspect of the invention, the interference optical system includes: a plurality of reference objects arranged at different distances from the object to be measured; dividing means for dividing the light beam from the light source into signal light reflected by the object to be measured in the plurality of depth regions, and a plurality of reference light beams passed through the plurality of reference objects; frequency shifting means for shifting frequencies of the plurality of reference light beams by different amounts; and superimposing means for superimposing the signal light passed through the object to be measured on the plurality of reference light beams passed through the plurality of reference objects with the frequencies being shifted by the frequency shifting means to produce the interference light.

Further, according to a third aspect of the present invention, in the optical image measuring apparatus according to the first or second aspect of the invention, the interference optical system includes a Michelson interferometer.

Further, according to a fourth aspect of the present invention, in the optical image measuring apparatus according to the second aspect of the invention, the detection system includes: intensity modulating means for periodically modulating an intensity of the produced interference light with a modulation frequency synchronous with a shift amount of the frequency to extract the interference light component corresponding to the modulation frequency from the interference light; and photo detector means for receiving the extracted interference light component and converting the extracted interference light component into an electrical signal to output the signal.

Further, according to a fifth aspect of the present invention, in the optical image measuring apparatus according to the fourth aspect of the invention, the intensity modulating means is a shutter for periodically cutting off the interference light with the modulation frequency.

Further, according to a sixth aspect of the present invention, in the optical image measuring apparatus according to the fourth aspect of the invention, the detection system further includes interference light dividing means for dividing the produced interference light into a plurality of interference light beams, and the intensity modulating means and the photo detector means are arranged on optical paths for the plurality of interference light beams divided.

Further, a seventh aspect of the present invention provides an optical image measuring apparatus, including: a light source for emitting a light beam; a first beam splitter for dividing the light beam from the light source into signal light reflected by an object to be measured in a plurality of depth regions, and reference light reflected by a predetermined reference object; a second beam splitter for dividing the reference light into a plurality of reference light beams; a plurality of frequency shifters arranged on optical paths for the plurality of reference light beams divided by the second beam splitter and adapted to shift frequencies of the plurality of reference light beams by different amounts; a plurality of reflector plates as the reference objects arranged on the optical paths for the plurality of reference light beams and at difference distances from the object to be measured; a third beam splitter for superimposing the plurality of reference light beams whose frequencies are shifted by the frequency shifters and which are reflected by the reflector plates on the signal light reflected by the object to be measured in the plurality of depth regions to produce interference light including a plurality of interference light components whose frequencies are different depending on the depth region thereof; and a shutter for cutting off the produced interference light with a frequency synchronous with any one of shift amounts of the frequencies to extract the interference light component corresponding to the synchronous frequency from the interference light; a CCD camera for receiving the extracted interference light component and converting the extracted interference light component into an electrical signal to output the signal; and a computer for calculating an intensity of the interference light component and a phase distribution based on the outputted electrical signal, and calculating a reflectance distribution of the object to be measured in the depth region corresponding to the interference light component based on the intensity and the phase distribution to form the image based on the reflectance distribution.

Note that in the present invention, the term "synchronous" in the phrase "(modulation) frequency synchronous with a shift amount of the frequency" implies that the (modulation) frequency is (substantially) equivalent to the shift amount, that the (modulation) frequency is n times larger than the shift amount, and that the (modulation) frequency is 1/n of the shift amount (where n is an integer of 2 or more).

In addition, the term "different" in the phrase "whose frequencies are different depending on the depth region" implies none of the conditions that the frequency corresponding to a given depth region is equal to, n times higher than, and 1/n of the frequencies corresponding to the other depth regions. Similarly, the term "different" in the phrase "shift the frequencies by different amounts" implies none of the conditions that the shift amount of a given frequency is equal to, n times larger than, nor 1/n of the shift amounts of the other frequencies.

The optical image measuring apparatus according to the present invention can take images of an object to be measured in each depth region in parallel by producing interference light including interference light components corresponding to each depth region thereof, selectively detecting each interference light component from the interference light, and forming an image of the object to be measured in the depth region corresponding to each interference light component.

BRIEF DESCRIPTION OF THE DRAWINGS

In the accompanying drawings:

FIG. 3(A) to FIG. 3(D) illustrate an example of a sampling mode of a first interference light component of inference light with the optical image measuring apparatus according to the present invention, in which FIG. 3(A) is a graph showing a time waveform of the first interference light component, FIG. 3(B) is a graph showing an example of a waveform of a first sampling for sampling the first interference light component, FIG. 3(C) is a graph showing an example of a waveform of a second sampling function for sampling the first interference light component, and FIG. 3(D) is a graph showing an example of a waveform of a third sampling function for sampling the first interference light component;

FIG. 4(A) to FIG. 4(D) illustrate an example of a sampling mode of a second interference light component of inference light with the optical image measuring apparatus according to the present invention, in which FIG. 4(A) is a graph showing a time waveform of the second interference light component, FIG. 4(B) is a graph showing an example of a waveform of a first sampling function for sampling the second interference light component, FIG. 4(C) is a graph showing an example of a waveform of a second sampling function for sampling the second interference light component, and FIG. 4(D) is a graph showing an example of a waveform of a third sampling function for sampling the second interference light component;

FIG. 5(A) to FIG. 5(D) illustrate an example of a sampling mode of an n-th interference light component of inference light with the optical image measuring apparatus according to the present invention, in which FIG. 5(A) is a graph showing a time waveform of the n-th interference light component, FIG. 5(B) is a graph showing an example of a waveform of a first sampling function for sampling the n-th interference light component, FIG. 5(C) is a graph showing an example of a waveform of a second sampling function for sampling the n-th interference light component, and FIG. 5(D) is a graph showing an example of a waveform of a third sampling function for sampling the n-th interference light component;

DETAILED DESCRIPTION OF THE PREFERRED EMBODIMENT

Hereinafter, an example of an optical image measuring apparatus according to an embodiment of the present invention will be described in detail with reference to the accompanying drawings.

(Structure of Apparatus)

Figure 1:
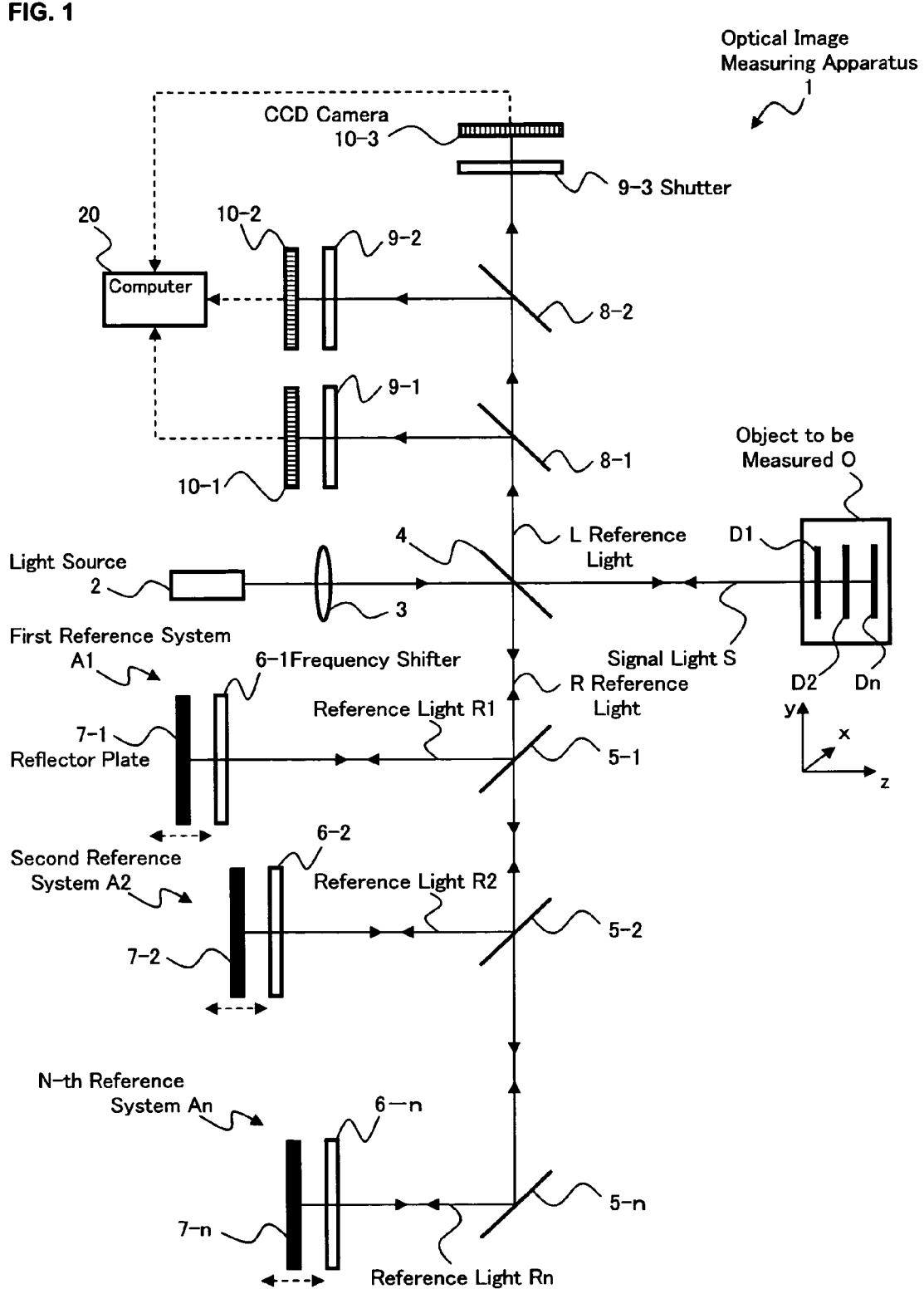
FIG. 1 is a schematic diagram showing an example of an optical image measuring apparatus according to the present invention.
Figure 2:
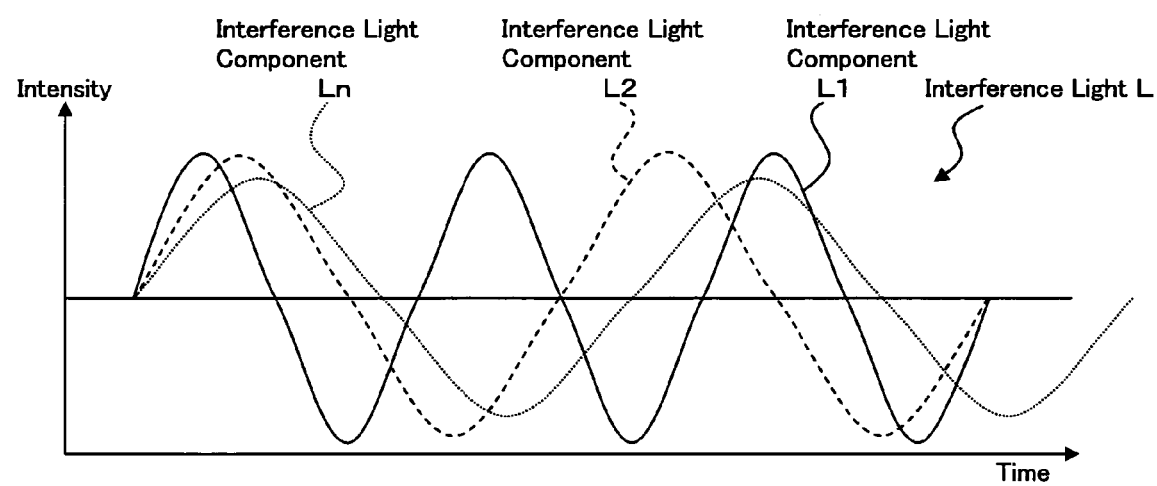
FIG. 2 is a graph showing a time waveform of interference light detected by the optical image measuring apparatus according to the present invention.
Figure 4:
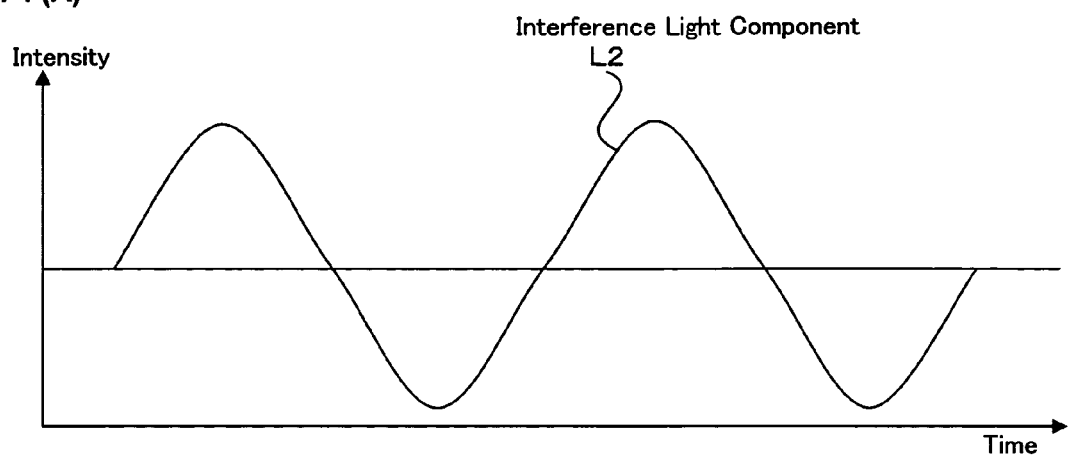
Figure 4:
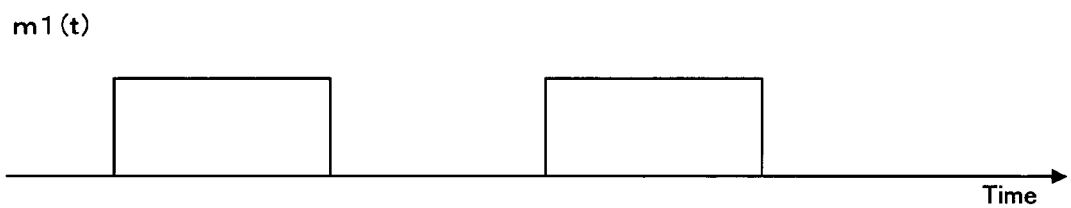
Figure 4:
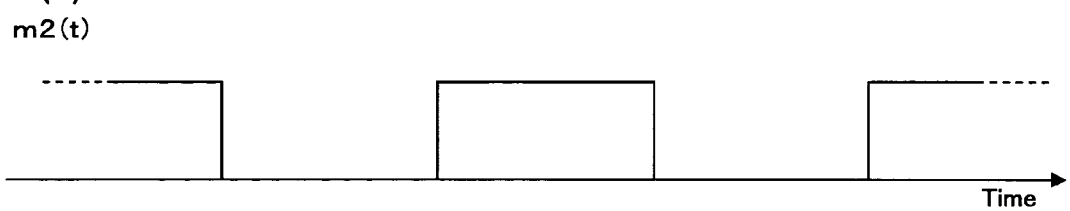
Figure 4:
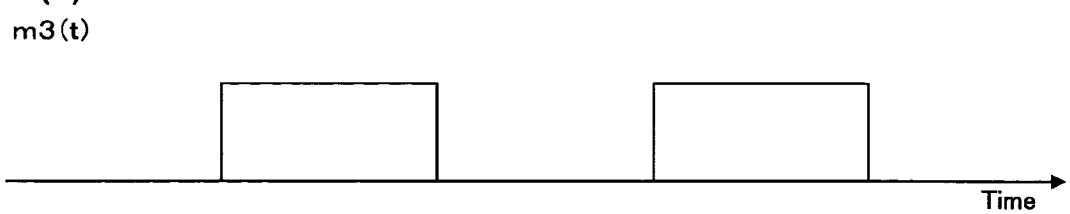
Figure 5:
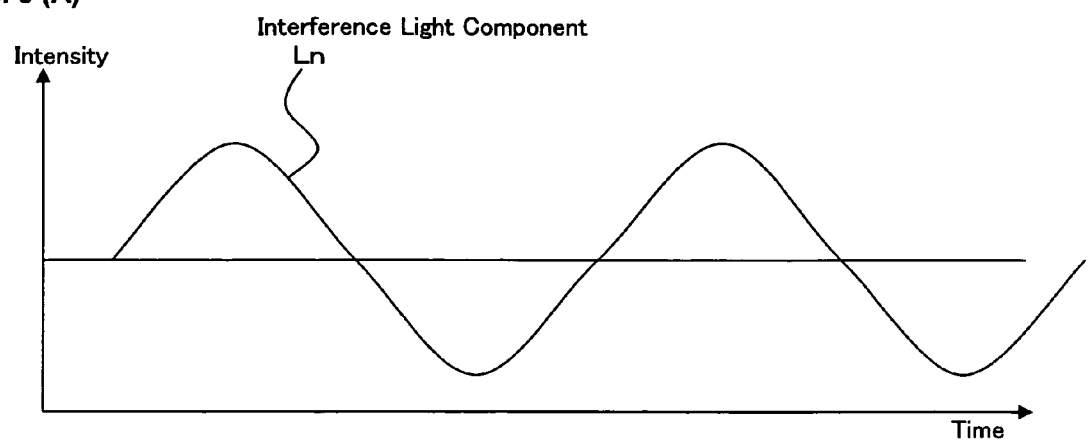
Figure 5:
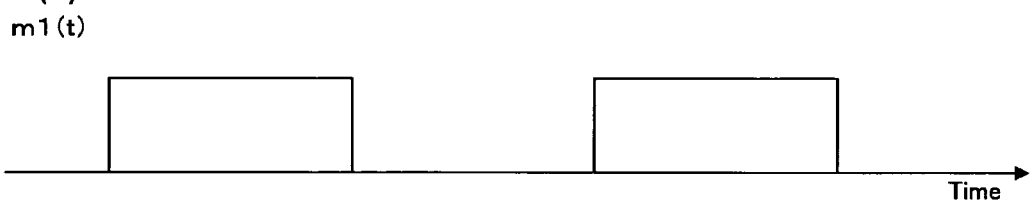
Figure 5:
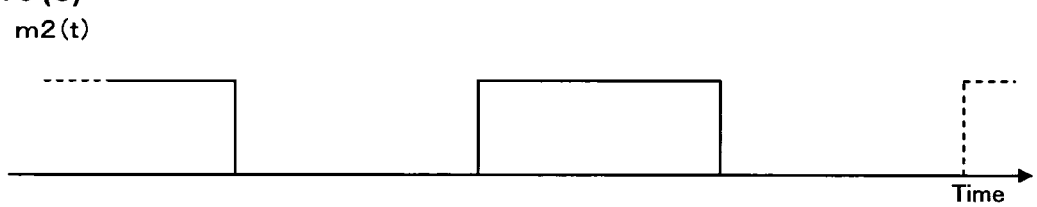
Figure 5:
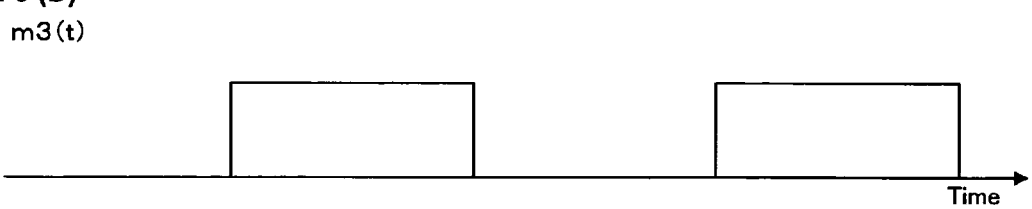
Figure 6:
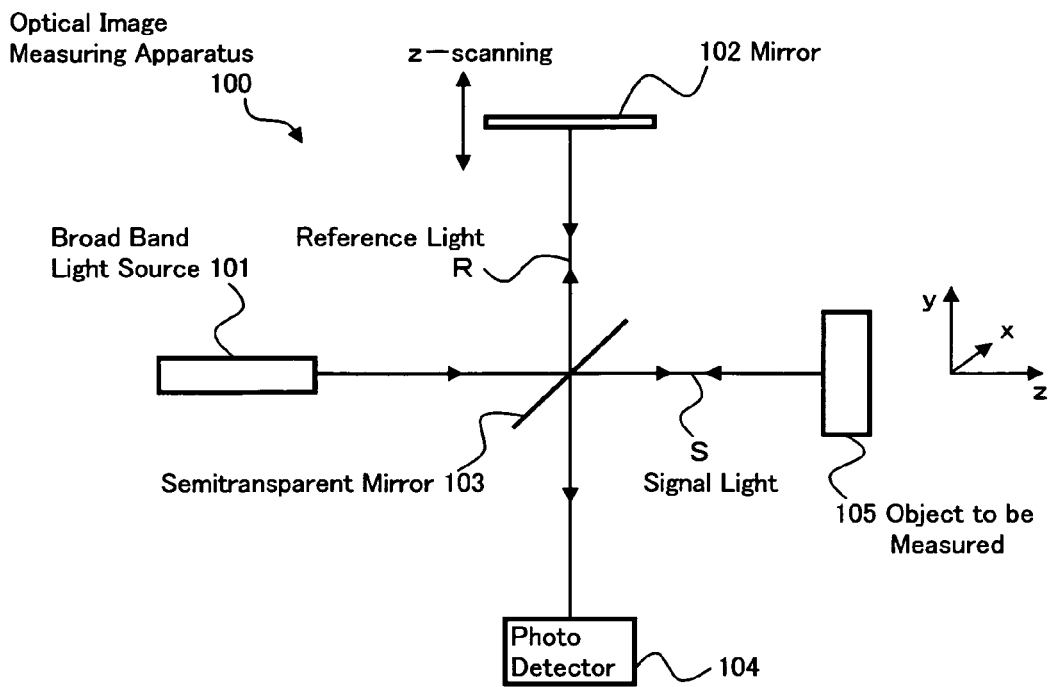
FIG. 6 is a schematic diagram showing a structure of a conventional optical image measuring apparatus.
Figure 7:
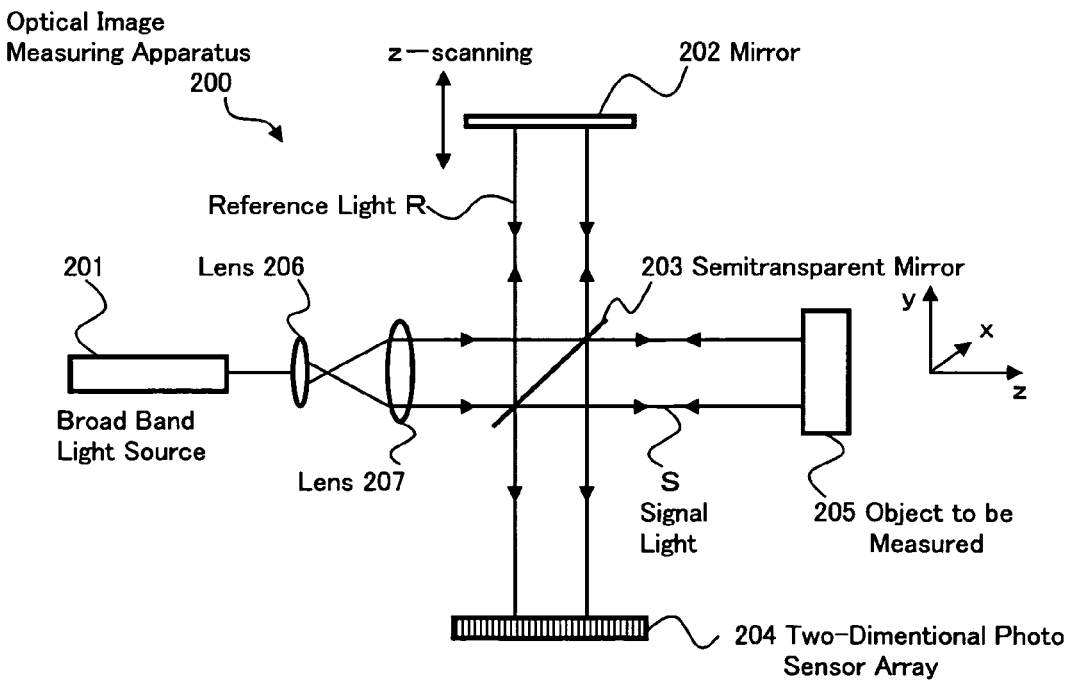
FIG. 7 is a schematic diagram showing a structure of a conventional optical image measuring apparatus.

FIG. 1 shows a schematic structure of an optical image measuring apparatus 1 according to a preferred embodiment of the present invention. The optical image measuring apparatus 1 is an apparatus usable in, for example, the medical and industrial fields, and has a structure for taking two-dimensional sectional images of an object to be measured O (hereinafter, referred to as "measuring object"), that is made of a scattering medium, in respective depth regions in parallel. Here, the depth region of the measuring object O means a region of the measuring object O at a given depth (depth position) (given z-coordinate in a three-dimensional coordinate system shown in FIG. 1). To be specific, the regions in question refer to regions defined by an area extending in an xy-plane direction at a given position in the depth direction (z-axis direction) of the measuring object O (i.e., given depth position) and predetermined areas in positions around the given depth position in the z-axis direction as denoted by D1 to Dn in FIG. 1). The predetermined areas in the z-axis direction define the width in the z-axis direction of the measuring object that is detectable by use of inference light L.

The optical image measuring apparatus 1 includes a broad band light source 2; a lens system 3; and a beam splitter 4. The wide band light source 2 is composed of an SLD, a light emitting diode (LED), or the like, and outputs a low-coherent continuous light beam. The lens system 3 converts the light beam from the light source 2 into a parallel light flux and increases a beam diameter thereof. The beam splitter 4 divides the light beam into signal light S and reference light R. The light source 2 can emit continuous light or pulsed light as appropriate. Note that a coherent length of a commercially available near-infrared region SLD is about 30 µm and a coherent length of an LED is about 10 µm. The signal light S is a light beam that propagates in an optical path passing through the measuring object O, and is reflected by the measuring object O in the plural depth regions D1 to Dn. The reference light R is a light beam that propagates in an optical path passing through predetermined reference objects (reflector plates 7-1 to 7-n as described later).

The optical image measuring apparatus 1 is provided with n reference systems, that is, a first reference system A1 to an n-th reference system An. The first reference system A1 includes a frequency shifter 6-1 and the reflector plate 7-1. The frequency shifter 6-1 is composed of an electro-optical modulator or acoustooptical modulator. The rest, that is, the second reference system A2 to the n-th reference system An are structured in the same way, where n is any integer of 2 or more.

Arranged on optical paths for the reference light beams R divided by the beam splitter 4 are a reflector 5-n and beam splitters 5-1 to 5-(n −1) that further divide the reference light R into n reference light beams R1 to Rn, and guide the respective divided reference light beams R1 to Rn to corresponding one of the first reference system A1 to the n-th reference system An, respectively. Note that, with the arrangement where the n-th reference system An is provided on the extension of the optical path for the reference light R, the reflector 5-n for reflecting the reference light passed through the beam splitter 5-(n −1) may be omitted.

Although not shown, a driving device is provided for moving the reflector plates 7-1 to 7-n independently of each other in the propagating direction of the reference light beams R1 to Rn (direction of the dotted arrow of FIG. 1). The respective reflector plates 7-1 to 7-n can adjust the distance to the measuring object O by being moved with the driving device. In measuring the measuring object O, the respective reflector plates 7-1 to 7-n are arranged in measurement positions apart from the measuring object O by different amounts (distances). The measurement positions of the respective reflector plates 7-1 to 7-n are determined in accordance with the depth (z-coordinate) of the corresponding one of the depth regions D1 to Dn of the measuring object O.

Further, it is possible to move the reflector plate 7-1 etc. in the direction of the dotted arrow of FIG. 1 with the above driving device to thereby cause the Doppler frequency shift of the reference light beam R1 etc. In this case, the frequency shifter 6-1 etc. may be omitted. Here, if a shift amount of the frequency of the reference light R (i.e., beat frequency of interference light) needs to be increased, the frequency shift caused by the frequency shifter 6-1 etc. and the Doppler frequency shift can be used together.

The reference light R produced by superimposing the reference light beams R1 to Rn passed through the respective reference systems A1 to An, and the signal light beams S reflected by the measuring object O in the respective depth regions D1 to Dn are superimposed on each other by the beam splitter 4 to thereby produce the interference light L. In short, the interference light L is produced by superimposing a part of the reference light R passed through the beam splitter 4 and a part of the signal light S reflected by the beam splitter 4.

Here, the beam splitter 4, the beam splitters 5-1 to 5-(n−1), the reflector 5-n, the frequency sifters 6-1 to 6-n, and the reflector plates 7-1 to 7-n constitute an "interference optical system" as referred to in the present invention. Further, the beam splitter 4, the beam splitters 5-11 to 5-(n−1), and the reflector 5-n constitute "dividing means" as referred to in the present invention, and the frequency shifters 6-1 to 6-n constitute "frequency shifting means". Further, the beam splitter 4 constitutes "superimposing means", a "first beam splitter", and a "third beam splitter" as referred to in the present invention. The optical image measuring apparatus 1 according to this embodiment is composed of a Michelson interferometer. The first and third beam splitters of the present invention share the beam splitter 4. If other interferometers such as a Mach-Zehnder interferometer are used, the first and third beam splitters may be of different types. In addition, the beam splitters 5-1 to 5-(n−1) constitute a "second beam splitter" as referred to in the present invention. In the optical image measuring apparatus 1, other optical elements such as an imaging lens group for focusing the interference light L into an image are arranged as appropriate, although not shown.

The interference light L produced by the beam splitter 4 is divided to form three optical paths with beam splitters 8-1 and 8-2. The interference light L propagating in each optical path is cut off with each predetermined frequency at regular intervals by high-speed shutters like a liquid crystal shutter, that is, shutters 9-1, 9-2, and 9-3, followed by sampling. The sampled interference light beams L are received by CCD cameras 10-1, 10-2, and 10-3 as storage-type two-dimensional optical sensor arrays. The respective CCD cameras 10-1, 10-2, and 10-3 subject the received interference light beams L to photoelectrical conversion into an electrical signal and output the resultant signal.

The shutters 9-1, 9-2, and 9-3 are not necessarily disposed immediately in front of the CCD cameras 10-1, 10-2, and 10-3, respectively. The shutters 9-1, 9-2, and 9-3 can be respectively disposed at arbitrary positions on respective optical paths joining branch points of the interference light beams L separated by the beam splitters 8-1 and 8-2 with the CCD cameras 10-1, 10-2, and 10-3. That is, the shutters 9-1, 9-2, and 9-3 may be disposed at positions in which the respective interference light beams L can be cut off to change the quantities of light beams received by the CCD cameras 10-1, 10-2, and 10-3 to 0.

Here, the beam splitters 8-1 and 8-2 constitute "interference light dividing means" as referred to in the present invention. Further, the shutters 9-1, 9-2, and 9-3 constitute "intensity modulating means" as referred to in the present invention. The CCD cameras 10-1, 10-2, and 10-3 constitute "photo detector means". Besides, the shutters 9-1, 9-2, and 9-3, and the CCD cameras 10-1, 10-2, and 10-3 constitute a "detection system" as referred to in the present invention.

Further, the optical image measuring apparatus 1 includes, as components for generating timing signals used for controlling open/close timings of the respective shutters 9-1, 9-2, and 9-3, a pulsed signal generator for generating pulsed signals, and a phase shifter for shifting the phases of the pulsed signals and outputting the timing signals to the respective shutters 9-1, 9-2, and 9-3. The phase shifters are provided for the shutters 9-1, 9-2, and 9-3 in a one-to-one correspondence, and shift the phases of the timing signals relative to the shutters 9-1, 9-2, and 9-3 independently. Hence, the shutters 9-1, 9-2, and 9-3 operate independently at respective timings.

The respective shutters 9-1, 9-2, and 9-3 periodically cut off the interference light beams L at predetermined frequencies, respectively, in response to the timing signals from the phase shifters in order to sample the respective interference light beams. Therefore, the respective CCD cameras 10-1, 10-2 and 10-3 periodically receive the corresponding interference light beams L, so each of the interference light beams is received as a periodic pulse train. At this time, the respective shutters 9-1, 9-2, and 9-3 are separately opened and closed, with the result that the pulses of the interference light beams L received by the CCD cameras 10-1, 10-2, and 10-3 have predetermined phase differences. The CCD cameras 10-1, 10-2, and 10-3 perform photoelectric conversion on the interference light beams L which are detected at each pixel and output heterodyne signals which are results obtained by the conversion to a computer 20. The heterodyne signal is an electrical signal reflecting the intensity and phase of the detected interference light beam.

The computer 20 executes a calculation process as mentioned later in response to a heterodyne signal outputted from the CCD cameras 10-1, 10-2, and 10-3. In addition, the computer 20 analyzes the calculation results to determine a reflectance distribution in the predetermined depth region of the measuring object O and form an image of the depth region based on the reflectance distribution. The formed image is displayed on a display device of a monitor device etc. (not shown) of the computer 20. The computer 20 includes a memory or storage device such as a ROM storing an arithmetic program for the above calculation process or a hard disk drive, and a CPU for executing the arithmetic program. The computer 20 constitutes "image forming means" as referred to in the present invention. Note that as the image forming means of the present invention, such a computer may be arranged outside a housing storing the optical structure or accommodated in the same housing.

(Measurement Form)

A measurement form of the optical image measuring apparatus 1 thus structured will be described next. First, an operator moves the reflector plates 7-1 to 7-n to positions where the measuring object O can be measured in the respective depth regions D1 to D3. More specifically, the reflector plates 7-1 to 7-n are arranged in positions where the reference light beams R1 to Rn interfere with the signal light beam S components reflected by the measuring object in the corresponding one of the depth regions D1 to Dn. That is, a reflector plate 7-k (k=1 to n) is arranged such that the distance of the reflector plate 7-k to the beam splitter 4 is substantially equal to the distance to a depth region Dk. Also, frequency shift amounts of the respective frequency shifters 6-1 to 6-n are set. The shift amounts may be manually set by the operator or set to predetermined default values. Besides, the frequency for the open/close operation of the shutters 9-1 to 9-n is set according to settings of the frequency shifters 6-1 to 6-n (details thereof will be described below).

A beam diameter of a light beam emitted from the light source 2 is increased by the lens system 3. The light beam is divided into the signal light S and the reference light R by the beam splitter 4.

The signal light S is made incident on the measuring object O and reflected by its surface or interior thereof. The reflected light includes components reflected by the measuring object O in the depth regions D1 to Dn. At this time, the measuring object O is made of a scattering medium, so the signal light S reflected by the measuring object O forms divergent wavefront with a random phase inclusive of multiplex-scattering. The signal light S passed through the measuring object O re-enters the beam splitter 4 of the measuring object O.

On the other hand, a part of the reference light R (reference light R1) is reflected by the beam splitter 5-1 to enter the first reference system A1. The reference light R1 passes through the frequency shifter 6-1 to be subjected to frequency shift, and then propagates to the reflector plate 7-1 and is reflected thereon. The reflected reference light R1 passes through the frequency shifter 6-1 again to be subjected to additional frequency shift and is made incident on the beam splitter 5-1 again. As described above, the frequency of the reference light R may be shifted by moving the reflector plate 7-1.

Apart (reference light R2) of the reference light R transmitted through the beam splitter 5-1 is reflected by the beam splitter 5-2 to enter the second reference system A2. The reference light R2 is transmitted through the frequency shifter 6-2 and its frequency is shifted. Then, the light is reflected by the reflector plate 7-2, and retransmitted through the frequency shifter 6-2 to have its frequency further shifted. After that, the light enters the beam splitter 5-2.

Similarly, a part (reference light Rk) of the reference light R is reflected by a beam splitter 5-$k$ ($k$=3 to n−1) to enter a k-th reference system Ak, and its frequency is shifted by the frequency shifter 6-$k$. After this, the light re-enters the beam splitter 5-$k$.

The reference light R (Rn) passed through the beam splitter 5-(n−1) is reflected by the reflector 5-$n$ to enter the n-th reference system An, and its frequency is shifted by the frequency shifter 6-$n$. Then, the light impinges on the reflector 5-$n$ again.

Here, the frequency shifters 6-1 to 6-$n$ shift the frequency by different shift amounts in relation to the reference light beams R1 to Rn. The shift amounts in which the frequency shifters 6-1 to 6-$n$ shift the frequency are preset.

The reference light beams R1 to Rn transmitted through the reference systems A1 to An are combined by use of the beam splitters 5-1 to 5-(n−1) and the reflector 5-$n$ to thereby re-enter the beam splitter 4. The composite light is also referred to as the reference light R. The reference light R is a light beam including the reference light beams R1 to Rn as frequency components, whose frequencies are shifted by different amounts.

The signal light S including components corresponding to the depth regions D1 to Dn of the measuring object O is superimposed on the reference light R including the reference light beams R1 to Rn as the frequency components by using the beam splitter 4 to produce the interference light L. At this time, the reflector plates 7-1 to 7-$n$ are arranged as mentioned above, so the signal light S component corresponding to the depth region Dk interferes with the frequency component Rk ($k$=1 to n) of the reference light R. Therefore, the interference light L contains: interference light L1 composed of a component corresponding to the depth region D1 and a frequency component R1; interference light L2 composed of a component corresponding to the depth region D2 and a frequency component R2; . . . ; and interference light Ln composed of a component corresponding to the depth region Dn and a frequency component Rn. The interference light beams L1 to Ln are referred to as "interference light components". The interference light components L1 to Ln may be regarded as a superimposed one of a DC component made up of background light of the interference light L and an AC component (beat signal) having a beat frequency.

The interference light L is divided into two by the beam splitter 8-1. A part of the interference light beam L is detected by the CCD camera 10-1 through the shutter 9-1.

The interference light L transmitted through the beam splitter 8-1 is further divided into two by the next beam splitter 8-2. A part of the interference light beam L is detected by the CCD camera 10-2 through the shutter 9-2.

The interference light beam L transmitted through the beam splitter 8-2 is detected by the CCD camera 10-3 through the shutter 9-3.

Here, it is desirable that an interference light dividing ratio of the beam splitter 8-1, that is, an intensity ratio between the transmitted interference light beam L and the reflected interference light beam L be 2:1. In other words, it is desirable that the beam splitter 8-1 transmit ⅔ of the incident light and reflect ⅓ thereof. In addition, it is desirable that an intensity ratio between the interference light beam L transmitted through the beam splitter 8-2 and the interference light beam L reflected thereon be 1:1. In other words, it is desirable that the beam splitter 8-2 transmit ½ of the incident light and reflect ½ thereof. Therefore, intensity levels of the interference light beams L detected by the CCD cameras 10-1, 10-2, and 10-3 are made equal to one another. This is suitable to perform calculation processing described later. An intensity ratio between the divided interference light beams is not limited to those and thus can be set as appropriate.

FIG. 2 and FIG. 3(A) to FIG. 5(D) are explanatory diagrams of a sampling form of the interference light L with the shutters 9-1, 9-2, and 9-3. FIG. 3(A) shows a time waveform of the interference light component L1 composed of the component corresponding to the depth region D1 and the frequency component R1. FIG. 3(B) to FIG. 3(D) each show an example of a sampling function for controlling an open/close operation of the shutters 9-1, 9-2, and 9-3. Each of the sampling frequencies of the sampling functions is set equal to or close to the frequency of the interference light component L1. Also, the frequency shifters 6-1 to 6-$n$ shift the frequencies by different amounts, so the interference light components L1 to Ln have different frequencies. Therefore, the shutters 9-1, 9-2, and 9-3 enable selective extraction of the interference light component L1 from the interference light L for sampling.

A sampling function shown in FIG. 3(B) is $m_1(t)$. The interference light beam L is sampled by periodically opening and closing (switching on and off) the shutter 9-1 based on the sampling function $m_1(t)$. The sampling function $m_1(t)$ has a waveform composed of, for example, a rectangular train with a duty of 50%, and as described above, its frequency $f_{sm}$ is set to a value equal to the frequency $f_{if}$ or close to the frequency $f_{if}$ (that is, $f_{sm}=f_{if}$ or $f_{sm}\approx f_{if}$).

The interference light component L1 is sampled over a phase range 0 to $\pi$ using the sampling function $m_1(t)$. A difference between the frequency $f_{sm}$ of the sampling function $m_1(t)$ and the beat frequency $f_{if}$ of the interference light component L1 which is indicated in the expression (1) ($\delta f=|f_{if}-f_{sm}|$) is set to a value sufficiently smaller than a response frequency of the CCD camera 10-1 serving as the storage type photo sensor. Therefore, a part of the interference light beam L1 having substantially the same phase is sampled during each period thereof. At this time, an output $i_1(t)$ from the CCD 10-1 that receives the interference light beam L1 is proportional to the amount of photocharge stored in the CCD 10-1 during a measurement period. More specifically, the output $i_1(t)$ is expressed by the following expression (2) (for example, see M. Akiba, K. P. Chan, and N. Tanno, Optics Letters, Vol. 28, 816 (2003))

$$i_1(t) = \langle K_1 i(t) m_1(t) \rangle \qquad (2)$$
$$= K_1 \left[ \frac{1}{2} I_s + \frac{1}{2} I_r + \frac{2}{\pi} \sqrt{I_s I_r} \cos(2\pi \delta f t + \phi) \right]$$

Here, <-> indicates a time average produced by a storage effect of the CCD 10-1. In addition, $\phi$ indicates an initial phase value for measurement and $K_1$ indicates photo detection efficiency including reflectance of the beam splitter 11 and a photoelectric conversion rate of the CCD 10-1.

Similarly, the interference light beam L2 is sampled by the shutter 9-2 whose open-and-close timings are controlled based on the predetermined sampling function $m_2(t)$ shown in FIG. 3(D), and is then detected by the CCD 10-2. The sampling function $m_2(t)$ has a waveform of a rectangular train with a duty of 50% and its frequency $f_{sm}$ is equal to that of the sampling function $m_1(t)$ for sampling the interference light beam L1. The sampling function $m_2(t)$ has a phase difference $\Delta\theta_{1,2}$ with the sampling function $m_1(t)$. The phase difference $\Delta\theta_{1,2}$ is caused by shifting amount predetermined by the phase shifter. Under the above-mentioned condition, the following output $i_2(t)$ is obtained from the CCD 10-2 based on the same fundamentals as the expression (2).

$$i_2 = K_2 \left[ \frac{1}{2} I_s + \frac{1}{2} I_r + \frac{2}{\pi} \sqrt{I_s I_r} \cos(2\pi\delta f t + \phi + \Delta\theta_{1,2}) \right] \quad (3)$$

Here, $K_2$ indicates photo detection efficiency including transmittance of the beam splitter 8-1, reflectance of the beam splitter 8-2, and a photoelectric conversion rate of the CCD 10-2.

As is apparent from the expressions (2) and (3), each of the outputs from the CCDs 10-1 and 10-2 includes the term of intensity $I_s$ of the signal light S and the term of intensity $I_r$ of the reference light R. In addition, the output from the CCD 10-1 includes the term related to an amplitude $\sqrt{I_s I_r}$ of the interference light beam L1 and a phase $(2\pi\delta f t + \phi)$ thereof. The output from the CCD 10-2 includes the term related to an amplitude $\sqrt{I_s I_r}$ of the interference light beam L2 and a phase $(2\pi\delta f t + \Delta\theta_{1,2})$ thereof.

Similarly, the interference light beam L1 is sampled by the shutter 9-3 whose open-and-close timings are controlled based on the sampling function $m_3(t)$ shown in FIG. 3(D), and is then detected by the CCD 10-3. The sampling function $m_3(t)$ has a waveform of a rectangular train with a duty of 50% and its frequency $f_{sm}$ is equal to that of the sampling function $m_1(t)$ for sampling the interference light beam L1. The sampling function $m_3(t)$ has a phase difference $\Delta\theta_{1,3}$ with the sampling function $m_1(t)$. The phase difference $\Delta\theta_{1,3}$ is caused by shifting amount predetermined by the phase shifter. At this time, the following output $i_3(t)$ is obtained from the CCD 10-3 based on the same fundamentals as the expression (2).

$$i_3 = K_3 \left[ \frac{1}{2} I_s + \frac{1}{2} I_r + \frac{2}{\pi} \sqrt{I_s I_r} \cos(2\pi\delta f t + \phi + \Delta\theta_{1,3}) \right] \quad (4)$$

Here, $K_3$ indicates photo detection efficiency including transmittance of each of the beam splitters 8-1 and 8-2, and a photoelectric conversion rate of the CCD 10-3.

The interference light components L2 and Ln shown in FIG. 4(A) to FIG. 5(D) are sampled on the basis of the same fundamentals, and detected by the CCD cameras 10-1, 10-2, and 10-3.

(Calculation Process)

The electrical signals outputted from the CCD cameras 10-1, 10-2, and 10-3 as represented by the expressions (2), (3), and (4) are transmitted to the computer 20. The computer 20 executes the following calculation using the output results, thereby calculating the DC component represented by the expression (1) corresponding to the background light of the interference light component L1, that is, the background light of the interference light L, the signal intensity of the interference light component L1, and the spatial phase distribution. The computer 20 calculates the reflectance distribution of the measuring object O in the depth region D1 corresponding to the interference light component L1 based on the intensity of the interference light component L1 and the phase distribution. Then, the computer executes the processing for forming the two-dimensional sectional image of the measuring object O in the depth region D1 based on the obtained reflectance distribution. Note that the image formation processing of the computer 20 based on the information on the intensity of the interference light component L1 and phase distribution is effected in the same way as in conventional apparatuses.

Here, as shown in FIG. 3(B), FIG. 3(C) and FIG. 3(D) the phase difference $\Delta\theta_{1,2}$ between the sampling function $m_1(t)$ and the sampling function $m_2(t)$ is set to $-\pi/2$. The phase difference $\Delta\theta_{1,3}$ between the sampling function $m_1(t)$ and the sampling function $m_3(t)$ is set to $\pi/2$. In this time, an intensity $S_1$ of the direct current component of the heterodyne signal which is composed of the background light of the interference light and phase quadrature components (sine component and cosine component) $S_2$ and $S_3$ thereof are expressed by the following respective expressions.

$$S_1 = \frac{i_2}{K_2} + \frac{i_3}{K_3} = I_s + I_r \quad (5)$$

Therefore, the intensity of the direct current component corresponding to the background light of the interference light L can be calculated based on the electrical signals from the two CCD cameras 10-2 and 10-3 of the three CCD cameras 10-1, 10-2, and 10-3.

$$S_2 = \frac{i_2}{K_2} - \frac{i_3}{K_3} = \frac{4}{\pi} \sqrt{I_s I_r} \sin(2\pi\delta f t + \phi) \quad (6)$$

$$S_3 = \frac{2i_1}{K_1} - S_1 = \frac{4}{\pi} \sqrt{I_s I_r} \cos(2\pi\delta f t + \phi) \quad (7)$$

When the expressions (6) and (7) are used, the amplitude of the interference light component L1 is expressed by the following expression.

$$\sqrt{I_s I_r} \propto \sqrt{S_2^2 + S_3^2} \quad (8)$$

Here, a proportionality factor related to the right side is $\pi/4$. The amplitude of the interference light component L1 can be calculated using the direct current component obtained by the expression (5). Therefore, when the direct current component is added to the amplitude of the heterodyne signal, the intensity of the heterodyne signal, that is, the intensity of the interference light component L1 can be obtained.

According to the optical image measuring apparatus 1, the spatial phase distribution of the interference light L1 can be obtained for imaging by the following measurement method.

When the interference components $S_2(t_1)$ and $S_3(t_1)$ of the heterodyne signal which are expressed by the expressions (6) and (7) are obtained at a measurement time $t=t_1$, the following signal is calculated from a ratio of both the interference components.

$$S_4 = \frac{S_2(t_1)}{S_3(t_1)} = \tan(2\pi \delta f t_1 + \phi) \quad (9)$$

As is apparent from the expression (9), a signal $S_4$ does not depend on the amplitude of the interference light L1 and includes only phase information thereof. Therefore, a phase $\phi(x, y, t_1)$ of the heterodyne signal which is detected and outputted from each of pixels of the CCDs 10-1, 10-2, and 10-3, each of which is the two-dimensional photo sensory array, is expressed by the following expression. Here, (x, y) indicates positional coordinates of each of the pixels on the CCDs.

$$\phi(x, y, t_1) = \tan^{-1}\left[\frac{S_2(x, y, t_1)}{S_3(x, y, t_1)}\right] - 2\pi \delta f t_1 \quad (10)$$

It can be assumed that the second term $2\pi\delta f t_1$ of the expression (10) is an instantaneous phase value of an alternating current signal having a frequency $\delta f$ of zero or substantially zero at a measurement time $t_1$ and kept constant regardless of the positions (that is, variables x, y) of the pixels of the CCDs 10-1, 10-2, and 10-3. A difference between a phase $\phi(x_1, y_1, t_1)$ of a heterodyne signal detected from a pixel located at coordinates $(x=x_1, y=y_1)$ on the CCDs 10-1, 10-2, and 10-3 and a phase of a heterodyne signal detected from each of the pixels is obtained. Therefore, a spatial distribution of the phase differences between the heterodyne signals, that is, a spatial phase distribution of the interference light L1 can be imaged. It is expected that such measurement of the spatial phase distribution of the interference light is effective for image measurement using phase difference values as references, for example, high precision measurement on a mirror surface, which is performed by a heterodyne interference method.

When the phase information is used, frequency information of the interference light L can be obtained. That is, a phase difference $\delta f$ between the frequency $f_{if}$ of the heterodyne signal and the sampling frequency $f_{sm}$ is calculated by using the following expression based on phases $\phi(x, y, t_1)$ and $\phi(x, y, t_2)$ obtained by calculation at two measurement times $t=t_1$ and $t=t_2$.

$$\delta f = \frac{1}{2\pi}\left|\frac{\phi(x, y, t_1) - \phi(x, y, t_2)}{t_1 - t_2}\right| \quad (11)$$

Because the sampling frequency $f_{sm}$ is known, the frequency $f_{if}$ of the heterodyne signal, that is, the frequency of the interference light L1 can be calculated based on a result calculated from the expression (11). It is expected that the heterodyne frequency measuring method is effectively usable for Doppler velocity measurement using the heterodyne interference method, such as blood flow measurement on a fundus of an eye to be examined.

The intensity and spatial phase distribution can be also calculated with respect to the interference light components L1 and Ln shown in FIG. 4(A) to FIG. 5(D) based on the same fundamentals.

The optical image measuring apparatus 1 of the above embodiment includes the shutters 9-1, 9-2, and 9-3 such as the high-speed shutters, as the intensity modulating means of the present invention. The intensity modulating means is not, however, limited thereto. For example, it is possible to provide an SLM (spatial light modulator) capable of periodically increasing/decreasing the transmittance at which the interference light is transmitted in place of such shutter means that completely blocks the interference light, thereby modulating the intensity of the interference light received by the photo detector means such as a CCD and sampling the interference light. That is, the shutter means switches the intensity of the interference light received by the photo detector means between 0 and 100 (maximum intensity); however, it is possible to adopt such a structure as to switch the intensity of the interference light periodically between 10 and 80, for example.

Further, in modulating the intensity of the interference light, it is possible to adopt a system for periodically switching the intensity among three or more values or a system for periodically, or successively switching the same between two values, according to the sampling form etc., instead of simply switching the intensity between the two values. Note that the intensity modulation range may be determined with the sensitivity of the CCD camera etc. taken into account. As the intensity modulating means of the present invention, any means may be employed insofar as the intensity of the interference light can be periodically modulated. The intensity modulating means and the photo detector means may be integrated.

The beam splitters 4, 5-1 to 5-(n−1), 8-1, and 8-2 of any form can be used, but a cubic beam splitter may disadvantageously allow the light reflected at the interface with the air to enter the CCD camera, so a plate- or wedge-like beam splitter is preferably used.

The three separate CCD cameras 10-1, 10-2, and 10-3 are provided in the optical image measuring apparatus 1. For example, a three-chip CCD camera (unit) such as 3-CCD type color CCD camera may be used and the intensity modulating means may be disposed in front of each of the CCD chips to construct an apparently single CCD camera. Therefore, it is possible to achieve the simplification of an apparatus structure, the inner space saving of the apparatus, and the like.

When a light receiving surface of a single CCD camera is divided into a plurality of regions and the intensity modulating means is disposed in front of each of the regions, it is also possible to detect the interference light using each of the regions of the CCD camera as a single CCD camera. At this time, a single intensity modulating means composed of, for example, a liquid SLM having a size necessary to cover the plurality of regions of the CCD camera may be disposed and a region of the intensity modulating means corresponding to each of the regions of the CCD camera may be controlled to detect the interference light. According to such a structure, it is possible to achieve the simplification of an apparatus structure and the inner space saving of the apparatus. In addition, it is unnecessary to perform sampling with synchronous control of a plurality of CCD cameras. Therefore, a control system can be simplified.

Offset adjustment of a direct current component of a charge stored in the CCD camera and gain adjustment of an alternating current signal may be suitably performed to improve the contrast of interference fringes caused by the detected interference light.

When a return mirror for two-reflection or a corner cube is applied as the reference object, a moving distance of the reference object can be shortened. Therefore, the inner space saving of the apparatus can be achieved. In addition, it is possible to reduce a load on the dividing device and the power consumption thereof when the reference object is moved.

The optical image measuring apparatus 1 sets a phase difference $\Delta\theta_{1,2}$ between the sampling function $m_1(t)$ and the sampling function $m_2(t)$ to $-\pi/2$, and sets a phase difference $\Delta\theta_{1,3}$ between the sampling function $m_1(t)$ and the sampling function $m_3(t)$ to $\pi/2$, thereby sampling each interference light component. However, the present invention is not limited thereto.

In the above-mentioned embodiment, the sampling of the interference light component is performed at the sampling frequency (substantially) equal to the beat frequency. However, the present invention is not limited to such sampling. For example, when a frequency which is an integral multiple of the beat frequency of the interference light component desired to be extracted is applied as the sampling frequency, each of a plurality of phase ranges of the interference light beam can be periodically sampled. According to such a method, the plurality of phase ranges can be sampled for each period of the interference light beam, so the interference light can be analyzed more precisely. Therefore, it can be expected to improve the measurement precision.

It is also possible to apply a sampling frequency which is an integral submultiple (1/n) of the beat frequency. According to such a method, a predetermined phase range of the interference light beam is sampled every n-period. Therefore, this method can be efficiently used in the case where the intensity changed by the intensity modulating means cannot follow the beat frequency.

It is preferable that the sampling function used for the optical image measuring apparatus of the present invention have the duty of 50%. This is because when the duty is smaller than 50%, the quantities of light received by the CCD cameras 10-1, 10-2, and 10-3 are decreased to reduce the detection efficiency of the interference light. On the other hand, when the duty ratio exceeds 50%, the detection efficiency also reduces. Note that, it is possible to use the sampling function having the duty ratio other than 50%.

With respect to the sampling function used for the optical image measuring apparatus of the present invention, in order to suitably control the open-and-close timings of the shutters 9-1, 9-2, and 9-3, it is preferable to use the rectangular waveform as shown in FIG. 3(B) to FIG. 3(D). Note that a sampling function having a waveform other than the rectangular wave, such as a sine wave or a triangular wave can be used as appropriate.

The optical image measuring apparatus according to the present invention is not limited to the structure in which the interference light is divided into the three optical paths as in the above-mentioned embodiment. The number of optical paths of the interference light beams is arbitrarily set. When the optical path of the interference light is divided into a plurality of optical paths, it is preferable to use a structure in which the photo detection means such as the CCD is provided on each of the optical paths and the intensity modulating means is provided on each of the optical paths except one optical path, or a structure in which the intensity modulating means is provided on each of optical paths. When the former structure is employed, the interference light component is successively detected by the photo detection means disposed on an optical path on which the intensity modulating means is not provided, to thereby calculate the direct current component corresponding to the background light of the interference light component. In addition to such structures, a structure in which the intensity modulating means is provided on an arbitrary number of optical paths of the plurality of divided optical paths of the interference light beams can be employed as appropriate according to a measurement method and a calculation method.

In addition to the CCD cameras 10-1, 10-2, and 10-3, for example, a line sensor including an integration circuit can be applied as the photo detection means in the optical image measuring apparatus according to the present invention. Various types of one-dimensional or two-dimensional devices having both a function for receiving the interference light beam and performing photoelectric conversion thereon and a function for storing charges caused by the received interference light beam can be used for the photo detection means in the present invention.

In the embodiment of the present invention as described above, the optical image measuring apparatus having the Michelson type interference optical system is described. It is also possible to use another interference optical system such as a Mach-Zehnder type interference optical system (for example, see JP 3245135 B).

An optical fiber (bundle) used as a light guide member is provided in a part of the interference optical system. Therefore, the degree of freedom of apparatus design can be improved, the apparatus can be made compact, or the degree of freedom of location of the measuring object can be improved (for example, see JP 3245135 B).

When applied to the ophthalmic field, for example, the optical image measuring apparatus of the present invention can take images corresponding to plural divided portions of the eye to be examined in parallel. For example, if the reflector plates 7-1, 7-2, and 7-3 are arranged for measurement in positions corresponding to the cornea, crystalline lens, and retina of the eye to be examined, the interference light components L1, L2, and L3 are converted into signals representative of information on the cornea, crystalline lens, and retina. Sampling is performed with a sampling frequency synchronous with each interference light component, whereby the two-dimensional sectional images of the cornea, crystalline lens, and retina can be obtained.

Further, the reflector plates 7-1, 7-2, and 7-3 are moved by a distance within which the interference light components interfere with each other to scan the cornea etc. in the depth direction, making it possible to take the image at high speed.

Also, the difference in length between the optical path passing through the first reference system A1 and the optical path passing through the second reference system A2 is set substantially equivalent to the thickness of the retina. In addition, it is also possible to automatically move the reflector plate for detecting the interference light component L2 under control after the interference light component L1 is detected. Hence, quick measurement of the front and rear surfaces of the retina is allowed. Note that, it is also possible to detect portions of the eye to be examined other than the retina or detect three or more interference light components in synchronization with one another.

The optical image measuring apparatus of the present invention can widen its applicable range to various medical or industrial applications aside from the above usage.

The above-mentioned detailed structures are merely examples of the optical image measuring apparatus according to the embodiment of the present invention. Thus, various modifications can be made without departing from the spirit of the present invention.

What is claimed is:

1. An optical image measuring apparatus, comprising:
   a light source for emitting a light beam;
   an interference optical system for producing, based on a signal light having a two-dimensional section obtained from the light beam from the light source which captures parallel points simultaneously, interference light including a plurality of interference light components whose frequencies are different depending on depth regions of an object to be measured, the signal light being obtained by reflection of light beam entering a two-dimensional area of the object to be measured, the interference light indicating a two-dimensional section of the object to be measured;

a detection system for selectively detecting the interference light components from the produced interference light; and an image forming means for forming two-dimensional images of the object to be measured in the depth regions corresponding to the interference light components based on the detected interference light components, the images indicating a two-dimensional section of the object to be measured.

2. An optical image measuring apparatus according to claim 1, wherein the interference optical system includes:

a plurality of reference objects movable along the traveling direction of the light beam, being arranged at different distances from the object to be measured;

dividing means for dividing the light beam from the light source into signal light reflected by the object to be measured in the plurality of depth regions, and a plurality of reference light beams passed through the plurality of reference objects;

frequency shifting means for shifting frequencies of the plurality of reference light beams by different amounts; and superimposing means for superimposing the signal light passed through the object to be measured on the plurality of reference light beams passed through the plurality of reference objects with the frequencies being shifted by the frequency shifting means to produce the interference light having beam diameters spreading along a plane perpendicular to the traveling direction, the interference light including alternate components having a beat frequency generated in accordance with movement of the reference object.

3. An optical image measuring apparatus according to claim 1, wherein the interference optical system includes a Michelson interferometer.

4. An optical image measuring apparatus according to claim 2, wherein the detection system includes:

intensity modulating means for periodically modulating an intensity of the produced interference light with a modulation frequency synchronous with a shift amount of the frequency to extract the interference light component corresponding to the modulation frequency from the interference light; and photo detector means for receiving the extracted interference light component and converting the extracted interference light component into an electrical signal to output the signal.

5. An optical image measuring apparatus according to claim 4, wherein the intensity modulating means is a shutter for periodically cutting off the interference light with the modulation frequency.

6. An optical image measuring apparatus according to claim 4, wherein:

the detection system further includes interference light dividing means for dividing the produced interference light into a plurality of interference light beams; and the intensity modulating means and the photo detector means are arranged on optical paths for the plurality of interference light beams divided.

7. An optical image measuring apparatus, comprising:

a light source for emitting a light beam;

a first beam splitter for dividing the light beam from the light source into signal light reflected by an object to be measured in a plurality of depth regions, and reference light reflected by a predetermined reference object;

a second beam splitter for dividing the reference light into a plurality of reference light beams;

a plurality of frequency shifters arranged on optical paths for the plurality of reference light beams divided by the second beam splitter and adapted to shift frequencies of the plurality of reference light beams by different amounts;

a plurality of reflector plates as the reference objects arranged on the optical paths for the plurality of reference light beams and at difference distances from the object to be measured;

a third beam splitter for superimposing the plurality of reference light beams whose frequencies are shifted by the frequency shifters and which are reflected by the reflector plates on the signal light reflected by the object to be measured in the plurality of depth regions to produce interference light including a plurality of interference light components whose frequencies are different depending on the depth region thereof; and a shutter for cutting off the produced interference light with a frequency synchronous with any one of shift amounts of the frequencies to extract the interference light component corresponding to the synchronous frequency from the interference light;

a CCD camera for receiving the extracted interference light component and converting the extracted interference light component into an electrical signal to output the signal; and a computer for calculating an intensity of the interference light component and a phase distribution based on the outputted electrical signal, and calculating a reflectance distribution of the object to be measured in the depth region corresponding to the interference light component based on the intensity and the phase distribution, to form the image based on the reflectance distribution.

8. An optical image measuring apparatus according to claim 2, wherein the interference optical system includes a Michelson interferometer.

* * * * *